(12) United States Patent  
Andersen et al.

(10) Patent No.: US 8,206,985 B2  
(45) Date of Patent: Jun. 26, 2012

(54) METHOD OF DETERMINING THE EFFECT OF A SPILL ON A MARINE ENVIRONMENT

(75) Inventors: Odd Kjetil Andersen, Stavanger (NO); Steinar Sanni, Stavanger (NO)

(73) Assignee: Biota Guard AS, Stavanger (NO)

( * ) Notice: Subject to any disclaimer, the term of this patent is extended or adjusted under 35 U.S.C. 154(b) by 337 days.

(21) Appl. No.: 12/162,342

(22) PCT Filed: Jan. 23, 2007

(86) PCT No.: PCT/NO2007/000023  
§ 371 (c)(1), (2), (4) Date: Jan. 7, 2009

(87) PCT Pub. No.: WO2007/086754  
PCT Pub. Date: Aug. 2, 2007

(65) Prior Publication Data  
US 2009/0226373 A1    Sep. 10, 2009

(30) Foreign Application Priority Data

Jan. 26, 2006   (NO) .................................. 20060439

(51) Int. Cl.  
*G01N 31/00*    (2006.01)  
*E02D 31/00*    (2006.01)
(52) U.S. Cl. ............... 436/3; 73/61.41; 405/54; 436/28; 436/29; 436/55; 436/73; 436/139; 588/260; 700/266; 702/19; 702/188
(58) Field of Classification Search ............ 73/40, 61.41, 73/432.1; 405/54; 436/3, 28–29, 55, 73, 436/139, 183; 588/260; 700/266; 702/19, 702/188  
See application file for complete search history.

(56) References Cited

U.S. PATENT DOCUMENTS 3,770,052 A    11/1973   Childers  
(Continued)

FOREIGN PATENT DOCUMENTS

DE    44 43 788 A1    6/1995  
(Continued)

OTHER PUBLICATIONS

Morgan, E. L. et al. Remote Data Transmission (Proceedings of the Vancouver Workshop, Aug. 1987), 1989, IAHS Publication No. 178, 97-103.*

(Continued)

*Primary Examiner* — Arlen Soderquist  
(74) *Attorney, Agent, or Firm* — Knobbe Martens Olson & Bear LLP

(57) ABSTRACT

A method of determining the effect of a spill on a marine environment, in which physical and chemical sensors are arranged with living organisms (4, 6) fitted with instruments, at an appropriate distance and position from the object (1) which is to be monitored, wherein the response of the living organism (4, 6), measured online in real time, is compared with known patterns of response, and where upstream and downstream measurements are compared to determine whether a change in response may be caused by a spill from the object, the significance of the real time measurements being validated through sampling of the organisms on a regular basis or as required, in order to analyze the effects on the health of the organisms, biomarkers, for the purpose of assessing the significance of the environmental effect.

10 Claims, 3 Drawing Sheets

U.S. PATENT DOCUMENTS

| | | | | |
|---|---|---|---|---|
| 4,084,543 | A * | 4/1978 | Pequegnat | 119/200 |
| 4,626,992 | A * | 12/1986 | Greaves et al. | 600/300 |
| 4,723,511 | A * | 2/1988 | Solman et al. | 119/224 |
| 4,888,703 | A * | 12/1989 | Baba et al. | 702/22 |
| 5,010,776 | A * | 4/1991 | Lucero et al. | 73/863.23 |
| 5,140,855 | A * | 8/1992 | Gruber | 73/432.1 |
| 5,469,144 | A * | 11/1995 | Gradzki et al. | 340/603 |
| 5,798,222 | A | 8/1998 | Goix | |
| 6,058,763 | A | 5/2000 | Shedd et al. | |
| 6,119,630 | A | 9/2000 | Lobsiger et al. | |
| 6,393,899 | B1 | 5/2002 | Shedd et al. | |
| 6,932,542 | B2 | 8/2005 | Chianis et al. | |
| 7,009,550 | B2 * | 3/2006 | Moeller-Jensen | 342/52 |
| 2002/0063629 | A1 | 5/2002 | Chuang | |
| 2003/0211041 | A1 | 11/2003 | Ezratty et al. | |
| 2004/0206162 | A1 | 10/2004 | Shedd et al. | |
| 2004/0257264 | A1 * | 12/2004 | Moeller-Jensen | 342/52 |
| 2005/0189115 | A1 | 9/2005 | Rytlewski et al. | |
| 2008/0217022 | A1 | 9/2008 | Deans | |
| 2009/0226373 | A1 * | 9/2009 | Andersen et al. | 424/9.2 |
| 2010/0274491 | A1 * | 10/2010 | Andersen et al. | 702/13 |

FOREIGN PATENT DOCUMENTS

| | | |
|---|---|---|
| DE | 198 48 230 A1 | 4/2000 |
| FR | 2 868 446 A1 | 10/2005 |
| GB | 2 385 833 A1 | 9/2003 |
| WO | WO 99/44057 A1 | 9/1999 |

OTHER PUBLICATIONS

Jenner, H. A. et al, Kema Scientific & Technical Reports 1989, 7, 91-98.*
Kramer, K. J. M. et al, Hydrobiologia 1989, 188/189, 433-443.*
Englund, V. P. M. et al, Water Research 1994, 28, 2219-2221.*
Lee, P. G., Aquacultural Enginerring 1995, 14, 205-227.*
Xie, Q. et al, Biology and Environment: Proceedings of the Royal Irish Academy 1995, 95B, 217-223.*
Sluyts, H. et al, Environmental Toxicology and Chemistry 1996, 15, 1317-1323.*
Borcherding, J. et al, Ecotoxicology 1997, 6, 153-165.*
Shezifi, Y, et al, Aquaculture Engineering 1997, 16, 253-259.*
Gerhardt A. et al, Environmental Science and Technology 1998, 32, 150-156.*
Israeli-Weinstein, D. et al, Aquaculture 1998, 165, 81-93.*
Nicholson, S., Marine Pollution Bulletin 1999, 39, 261-268.*
Markich, S. J. et al, Aquatic Toxicology 2000, 51, 155-175.*
Tahedl, H. et al, Ecotoxicology and Environmental Safety B Environmental Research 2001, 48, 161-169.*
Kadar, E. et al, Aquatic Toxicology 2001, 55, 137-148.*
Van der Schalie, W. H. et al, Biosensors & Bioelectronics 2001, 16, 457-465.*
De Pirro, M. et al, Marine Pollution Bulletin 2001, 42, 1390-1396.*
Chelazzi, G. et al, Marine Environmental Research 2004, 58, 83-93.*
Scott, G. R. et al, Aquatic Toxicology 2004, 68, 369-392.*
Craig, S. et al, Water Research 2004, 38, 2144-2154.*
Liao, C.-M. et al, Environmental Pollution 2005, 41-52.*
Al-Arabi et al., "Contaminant Accumulation and Biomarker Responses in Caged Fish Exposed to Effluents from Anthropogenic Sources in the Kamaphuly river, Bangladesh", Environmental Toxicology and Chemistry, 24(8):1968-1978 (2005).
Cairns et al., "A Preliminary Report on Rapid Biological Information Systems for Water Pollution Control", Journal WPCF, 42(5):685-703 (1970).
De Flora et al., "Multiple Genotoxicity Biomarkers in Fish Exposed in Situ to Polluted River Water", Mutation Research, 319:167-177 (1993).
Foster et al., "Use of Freshwater Mussels to Monitor Point Source Industrial Discharges", Environmental Science and Technology, 12(8):958-962 (1978).
Gruber et al., "Industrial Effluent Monitoring Incorporating a Recent Automated Fish Biomonitoring System", Water, Air and Soil Pollution, 15:471-481 (1981).
Morgan et al., "Remote Sensing from Automated Biomonitoring Stations: New Developments in Water Quality Management", ASB Bulletin, 25(2):46-47 (1978).
Nelms et al., "BeRM: Bioelectric Response Monitor", Proc. Southeast Conference, 1:91-94 IEEE (1992).
Newsletter from RF-Akvamiljø, News No. 4, pp. 1-4 (2005).
Westlake, "Instream Biomonitoring of Industrial Wastewater Effluents." The Virginia Journal of Science, 26(2):78 (1975).
Johnson, K.S. et al. 2005 "Chemical sensor networks for the aquatic environment" Chem Rev 107: 623-640.

* cited by examiner

METHOD OF DETERMINING THE EFFECT OF A SPILL ON A MARINE ENVIRONMENT

This application is U.S. National Phase of International Application PCT/NO2007/000023, filed Jan. 23, 2007 designating the U.S., and published in English as WO 2007/086754 on Aug. 2, 2007, which claims priority to Norwegian Patent Application No. 20060439, filed Jan. 26, 2006.

This invention regards a method of determining the effect of a spill on a marine environment. More particularly, it regards a method in which living organisms are placed at an appropriate distance and position from an object to be monitored, and where the living organisms are fitted with instruments for physiological and behavioural measurements and are monitored in real time to register spills. The online signals from the instruments are compared with physical and chemical measurements of water quality and the known behavioural pattern of the organism to detect the occurrence of an accidental spill, and to determine whether the effect of the spill on the marine environment exceeds a predefined acceptable limit. If the online monitoring indicates a probability of unexpected spills or spills that exceed the accepted limit, the measurements are validated by taking samples of the organisms to measure their state of health.

Spills from port facilities, offshore installations and ships can cause damage to the local marine environment, which damage may take a long time to rectify. Although so-called "zero discharge" may be the aim, with "zero discharge" being defined as no discharges to the sea or no discharges of substances that are harmful to the environment, accidental spills may occur, and knowing the effect of the spill on the surrounding marine environment will be of great importance when it comes to determining the severity of the spill and deciding on what, if any, action to take. In addition, it would be of interest to be able to prove that the effect of any permitted discharges is no greater than that which is already anticipated.

In most marine environments there is so-called background pollution which may be natural or may have been brought into the area from other areas.

Thus, when a spill occurs, it will be difficult to determine whether measurement values from samples taken after the spill represent background pollution or the present spill. In addition, these measuring results will generally not be available for quite a while after the spill has occurred, and so will not help to detect the spill while it is happening.

The object of the invention is to remedy or reduce at least one of the drawbacks of prior art.

The object is achieved in accordance with the invention, by the characteristics stated in the description below and in the following claims.

In a method of determining the effect of a spill on a marine environment physical and chemical sensors and living organisms fitted with instruments are placed at an appropriate distance and position from the object to be monitored, where the response of the living organism, measured online in real time, is compared with known behavioural patterns, and where upstream and downstream measurements are compared to determine whether a change in response may be caused by a spill from the object, the significance of the real time measurements being validated through sampling of the organisms on a regular basis or as required, in order to analyze the effects on the health of the organisms, biomarkers, for the purpose of assessing the significance of the environmental effect.

In this context, the term "living organisms fitted with instruments" refers to organisms that are fitted with sensors which can measure changes in physiology and behaviour.

As a result it becomes possible to detect a spill while it is happening, and by so doing, it also becomes possible to stop an accidental spill.

The invention allows monitoring of the response of living organisms to a spill. With this one can determine the effect of a spill on the marine environment, and also whether the effect exceeds an acceptable limit.

Furthermore, the extent of the harm caused, both by accidental and permitted discharges, can be assessed. It also becomes possible to evaluate the consequences of repeated spills and the cumulative effect of these.

Typically, a plurality of submerged cages is arranged in a pattern by or around the object to be monitored. The living organism(s) are in the cage and are fitted with the required measuring devices.

The living organisms are monitored by online instrumentation to measure physiological responses to external influences such as pollution. The choice of instrumentation is dependent on e.g. the site of the monitoring, climate and which organisms are the most appropriate for use in a given situation. If the living organism is in the form of shells, it would be appropriate to monitor the opening and closing of the shell, as it has been demonstrated that shells will close when exposed to a certain amount of pollution.

Basically, there are no limitations on which organisms one can select for such monitoring. The organism is selected based on the environment to be monitored. It may be appropriate to use fish and also various species of crustaceans or shellfish, or combinations of these as the living organism.

The physiological responses are compared with known patterns of response, and the upstream response is compared with the response measured downstream of the object to be monitored. This makes it possible to establish whether the effect is caused by the monitored object or another source.

In order to validate the significance of real time responses, which will principally indicate the potential for damage to the environment, the organisms are sampled on a regular basis or as required in order to validate the state of the organisms' health by use of diagnostic methods, also known as biomarkers, in order to reveal more permanent damage to the organisms.

It has been found that both fish and shells react to pollution with a change in heart rate. Thus it may be appropriate to measure the heart rate of the living organism, among other things because it provides an indication of the food intake of the organism.

Advantageously several measurements may be performed simultaneously, as the development in several separate biomarkers may provide important information when seen as a whole.

The measured values from the living organisms are transmitted to a measuring station which may be located on the object to be monitored, or somewhere else, by means of e.g. a wireless connection.

The measured values arriving at the measuring station can be recorded and assessed manually or by means of equipment that is known per se, and which may for instance trigger an alarm if a predetermined level of measurements or pattern of measurements occurs.

As distinct from prior art methods, in which living organisms in the area must be sampled on a regular basis, the invention requires such sampling only when an indication of a spill exists.

The following describes a non-limiting example of a preferred method illustrated in the accompanying drawings, in which.

Figure 1:
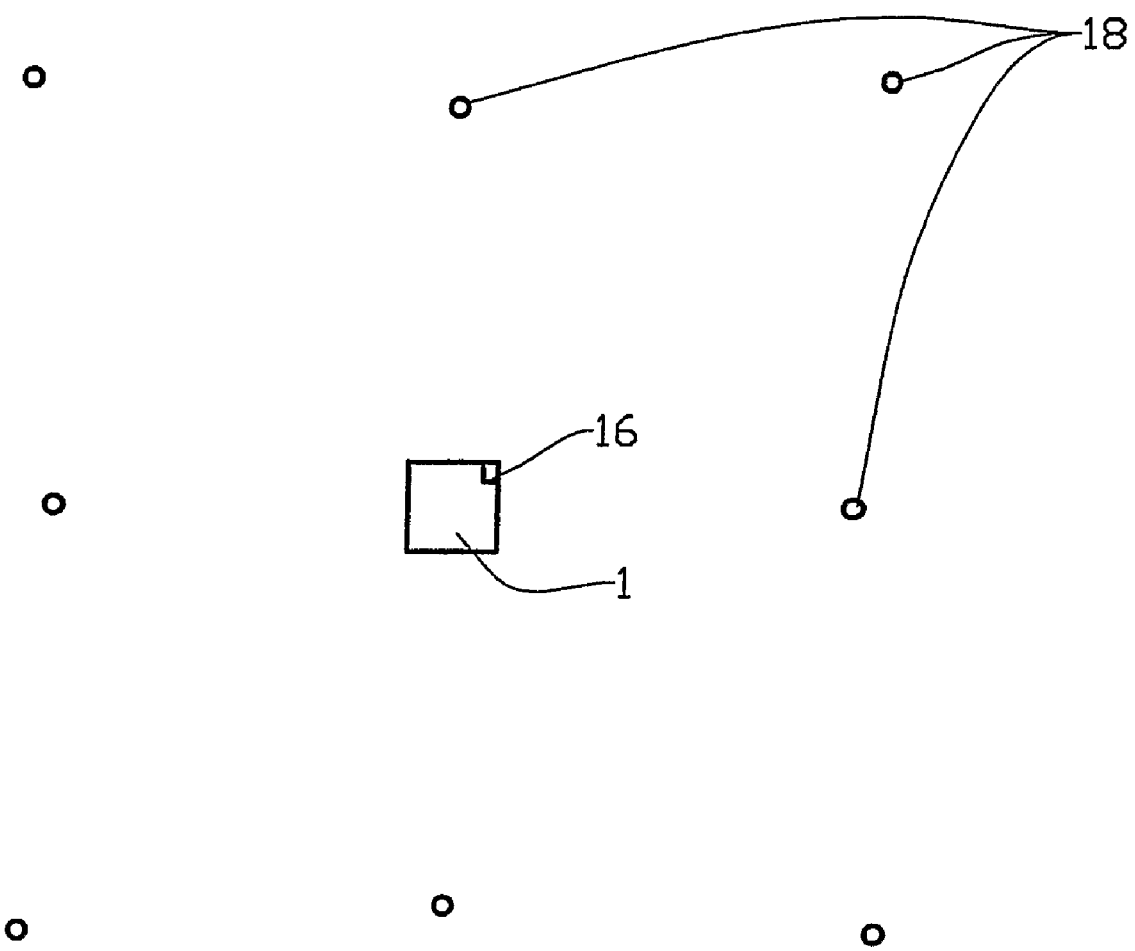
FIG. 1 is a schematic plan view of a vessel provided with monitoring equipment to carry out the method of the invention.
Figure 2:
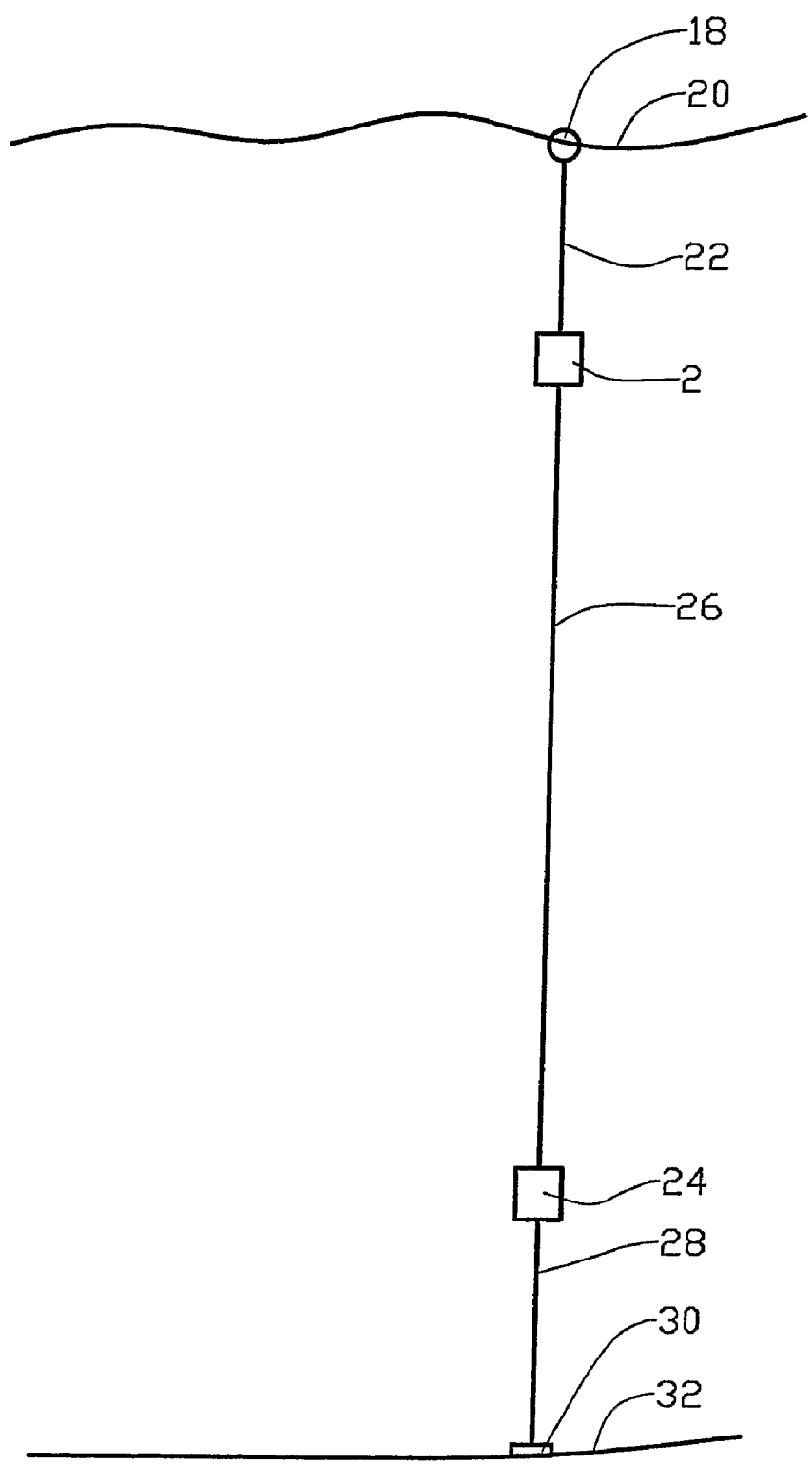
FIG. 2 is a schematic view of a suspension with a submerged cage for living organisms.
Figure 3:
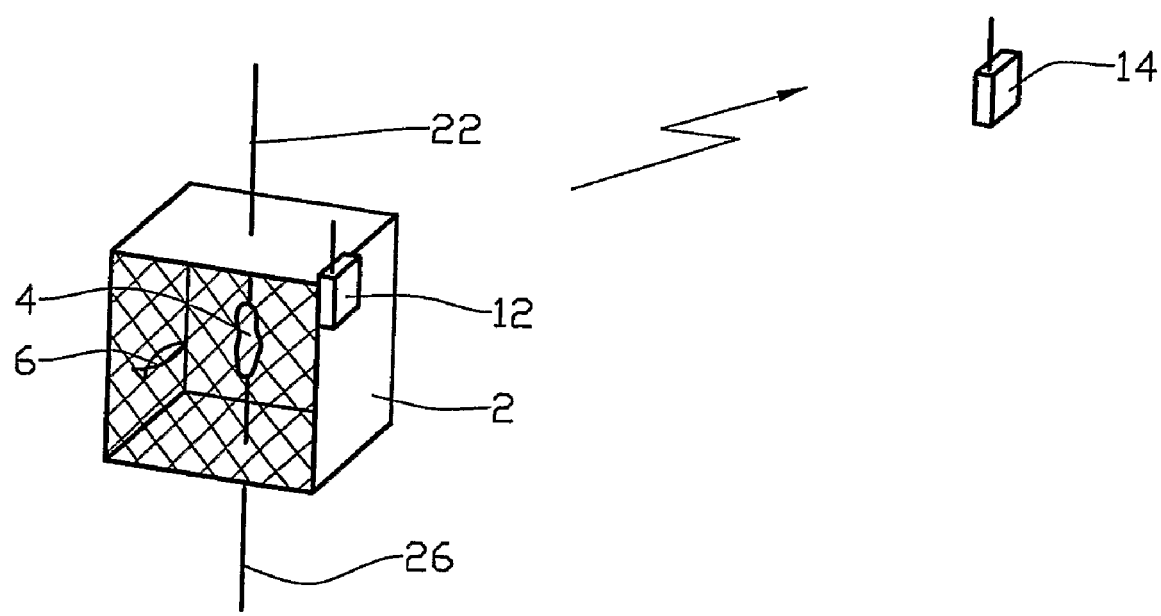
FIG. 3 is a larger scale schematic view of a cage in FIG. 2.
Figure 4:
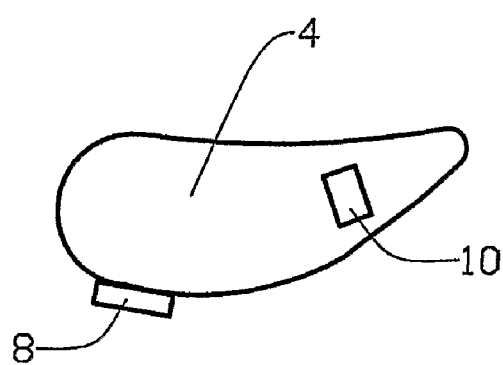
FIG. 4 is a schematic view of a blue mussel fitted with sensors, on an even larger scale.

In the drawings, reference number 1 denotes an object to be monitored. The object may be e.g. a port area or a floating or fixed offshore installation.

A plurality of flow-through cages 2 form habitats for living organisms in the form of shellfish 4 or fish 6.

The shellfish 4, in this case a shell (bivalve), is fitted with a first sensor 8 that reads whether the shell 4 is open or shut. A second sensor 10 is arranged to read the heart rate of the shell 4. Preferably the fish 6 is in an electrical field that allows measuring of the heart rate, among other things.

The sensors 8 and 10 communicate via links (not shown) to a first communication module 12 attached to the cage 2.

Preferably the first communication module 12 has wireless communication with a second communication module 14 typically located at a measuring station 16. Preferably the measuring station 16, where the incoming measurements are monitored and analyzed, is located on the object 1.

The cage 2 is connected to a float 18 on or below the surface of the sea 20 via a float rope 22. This preferred embodiment includes a second lower cage 24 in addition to the cage 2 which is located relatively near the surface of the sea 20. The cages 2, 24 are interconnected by an intermediate rope 26. An anchor line 28 connects the second cage 24 to an anchor 30 located on the seabed 32.

What is claimed is:

1. A method of determining whether a spill into a marine environment is from a particular offshore installation comprising:

(a) submerging a plurality of cages around and at distances from said installation, said cages containing living organisms fitted with sensors that monitor physiological or behavioral responses by said organisms;

(b) transmitting online, real-time signals to a measuring station;

(c) comparing signals from said cages to each other and to known patterns of response of said organisms; and (d) determining whether a response by said organisms is caused by a spill from said installation based on temporally different responses at each cage, thereby discriminating from a response caused by another source or by background pollution.

2. The method as claimed in claim 1 wherein said cages are provided with physical and chemical sensors.

3. The method as claimed in claim 1 wherein the significance of the real-time signals is validated by sampling of said organisms.

4. The method as claimed in claim 1 wherein said signals are compared to determine whether a spill from said installation having an effect on said environment exceeds a predefined limit.

5. The method as claimed in claim 1 wherein said signals are compared to determine the degree of damage to said environment by permitted discharges from said installation.

6. The method as claimed in claim 1 wherein said organisms comprise shellfish.

7. The method as claimed in claim 6 wherein said sensors monitor the shell opening and closing of said shellfish.

8. The method as claimed in claim 1 wherein said organisms comprise fish.

9. The method as claimed in claim 1 wherein said sensors monitor the heart rate of said organisms.

10. The method as claimed in claim 1 wherein said sensors monitor the food intake of said organisms.

* * * * *